United States Patent [19]
Yoon

[11] Patent Number: 5,571,134
[45] Date of Patent: Nov. 5, 1996

[54] SAFETY PENETRATING INSTRUMENT WITH PENETRATING MEMBER AND SAFETY MEMBER MOVING DURING PENETRATION AND TRIGGERED SAFETY MEMBER PROTRUSION

[76] Inventor: InBae Yoon, 2101 Highland Ridge Dr., Phoenix, Md. 21131

[21] Appl. No.: 327,686

[22] Filed: Oct. 24, 1994

Related U.S. Application Data

[63] Continuation-in-part of Ser. No. 83,220, Jun. 24, 1993, Pat. No. 5,431,635, and a continuation-in-part of Ser. No. 83,728, Jun. 29, 1993, Pat. No. 5,466,224, and a continuation-in-part of Ser. No. 115,152, Sep. 2, 1993.

[51] Int. Cl.⁶ ............................................. A61M 5/00
[52] U.S. Cl. ........................... 606/185; 604/165; 604/170
[58] Field of Search .................... 604/95, 158, 162, 604/163, 164, 165, 170, 272, 274, 280, 169; 606/167, 171, 185; 128/751, 752, 753, 754

[56] References Cited

U.S. PATENT DOCUMENTS

| | | |
|---|---|---|
| 1,087,845 | 2/1914 | Stevens . |
| 1,213,001 | 1/1917 | Philips . |
| 1,248,492 | 12/1917 | Hill . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran . |
| 4,254,762 | 3/1981 | Yoon . |
| 4,345,589 | 8/1982 | Hiltebrandt . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,828,547 | 5/1989 | Sahi et al. . |
| 4,869,717 | 9/1989 | Adair . |
| 4,902,280 | 2/1990 | Lander . |
| 4,931,042 | 6/1990 | Holmes et al. . |
| 4,943,280 | 7/1990 | Lander . |
| 5,030,206 | 7/1991 | Lander . |
| 5,053,016 | 10/1991 | Lander . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |

(List continued on next page.)

FOREIGN PATENT DOCUMENTS

| | | |
|---|---|---|
| 2544262 | 4/1977 | Germany . |
| 878265 | 11/1981 | U.S.S.R. . |
| 897224 | 1/1982 | U.S.S.R. . |
| 1435246 | 11/1988 | U.S.S.R. . |
| 904635 | 8/1962 | United Kingdom . |
| 9304632 | 3/1993 | WIPO . |
| 9304715 | 3/1993 | WIPO . |
| 9304716 | 3/1993 | WIPO . |
| 9317626 | 9/1993 | WIPO . |

*Primary Examiner*—Guy V. Tucker

[57] ABSTRACT

A safety penetrating instrument for penetrating an anatomical cavity wall to gain access to an anatomical cavity includes a distally-biased penetrating member and a distally-biased safety member, both of which are movable proximally in relation to a housing during penetration of the anatomical cavity wall. Upon penetrating into the anatomical cavity, an extending mechanism moves a cannula and/or the safety member distally relative to the housing in order to protect the distal end of the penetrating member. Extension or protrusion of the cannula and/or the safety member can be triggered by distally-biased movement of the safety member and/or the penetrating member upon entering the anatomical cavity.

32 Claims, 9 Drawing Sheets

U.S. PATENT DOCUMENTS

| | | |
|---|---|---|
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 11/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 3/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |
| 5,431,635 | 7/1995 | Yoon ....................................... 604/165 |

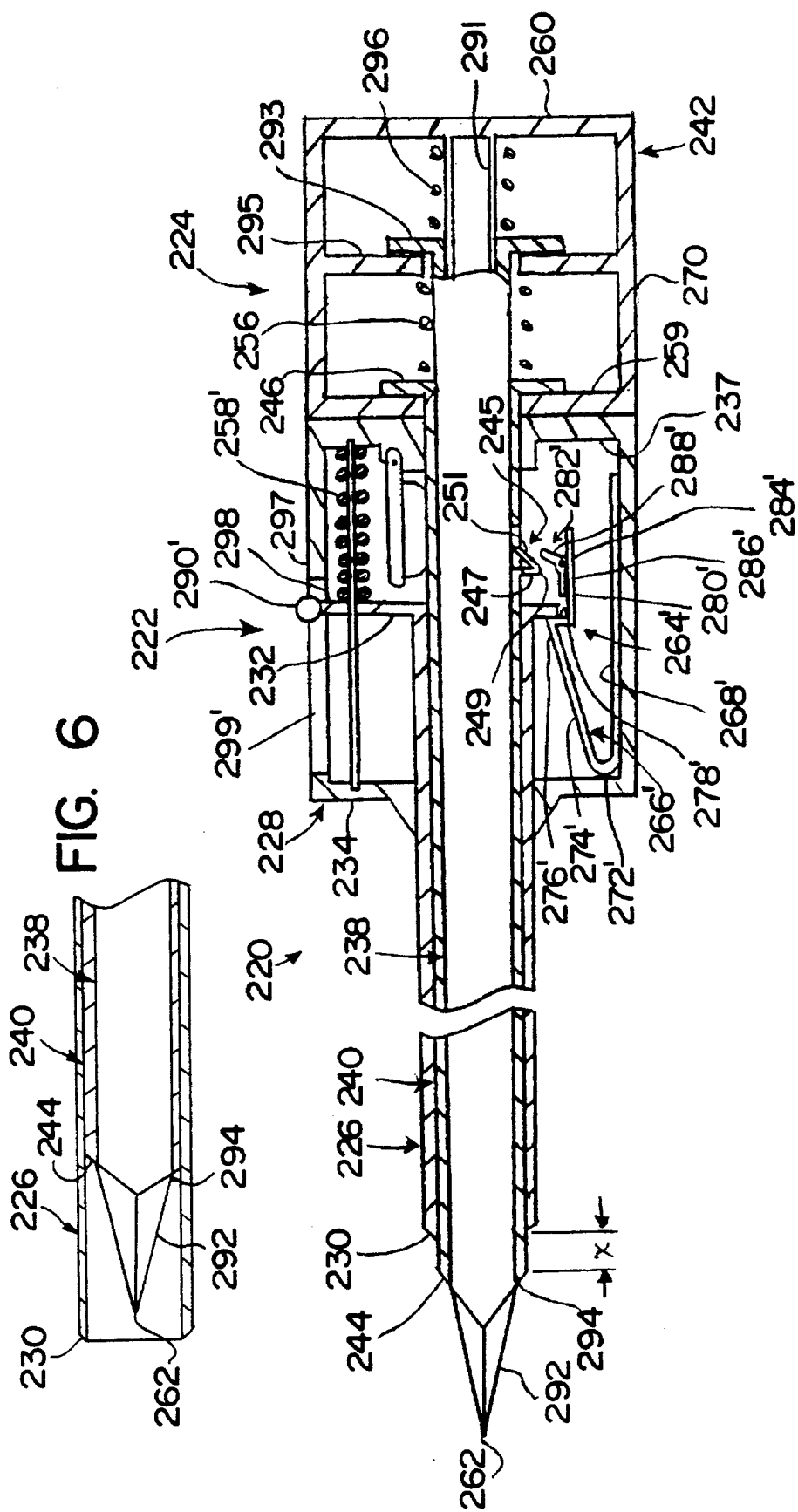

SAFETY PENETRATING INSTRUMENT WITH PENETRATING MEMBER AND SAFETY MEMBER MOVING DURING PENETRATION AND TRIGGERED SAFETY MEMBER PROTRUSION

CROSS-REFERENCE TO RELATED APPLICATIONS

This application is a continuation-in-part of prior applications Ser. No. 08/083,220, filed Jun. 24, 1993, now U.S. Pat. No. 5,431,635 Ser. No. 08/083,728, filed Jun. 29, 1993, now U.S. Pat. No. 5,466,224, and Ser. No. 08/115,152, filed Sep. 2, 1993, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments of the type having a penetrating member and a safety member biased distally to protrude beyond the distal end of the penetrating member by easing penetration and assuring protrusion of the safety member.

Another object of the present invention is to reduce the force-to-penetrate required to penetrate an anatomical cavity wall with a safety penetrating instrument of the type having a distally biased safety member for protruding beyond a distal end of a penetrating member once penetration into the cavity has been achieved.

A further object of the present invention is to increase the force biasing a safety member distally in a safety penetrating instrument to assure protrusion of the safety member after penetration into an anatomical cavity without increasing the force-to-penetrate required for penetration.

The present invention has an additional object to permit proximal movement of the penetrating member and safety shield or probe of a safety penetrating instrument during penetration of an anatomical cavity wall and to utilize the safety shield or probe as a safety member triggered to move distally from a retracted position exposing the distal end of the penetrating member to an extended protruding position covering the penetrating member distal end in response to distally-biased movement of the safety shield or probe upon entering the anatomical cavity.

Another object of the present invention is to permit proximal movement of the penetrating member and safety shield or probe of a safety penetrating instrument during penetration of an anatomical cavity wall and to utilize the safety shield or probe as a safety member triggered to move distally from a retracted position exposing the distal end of the penetrating member to an extended protruding position covering the penetrating member distal end in response to distally-biased movement of the penetrating member upon entering the anatomical cavity.

Yet another object of the present invention is to permit proximal movement of the penetrating member and safety shield or probe of a safety penetrating instrument during penetration of an anatomical cavity wall and to utilize the safety shield or probe as a safety member triggered to move distally from a retracted position exposing the distal end of the penetrating member to an extended protruding position covering the penetrating member distal end in response to distally-biased movement of both the penetrating member and safety shield or probe upon entering the anatomical cavity.

An additional object of the present invention is to permit proximal movement of the penetrating member and safety shield or probe of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of the safety shield or probe upon entering the anatomical cavity.

Still another object of the present invention is to permit proximal movement of the penetrating member and safety shield or probe of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of the penetrating member upon entering the anatomical cavity.

Yet a further object of the present invention is to permit proximal movement of the penetrating member and safety shield or probe of a safety penetrating instrument during penetration of an anatomical cavity wall and to utilize the cannula as a safety member triggered to move distally from a retracted position exposing the distal end of the penetrating member to an extended protruding position covering the penetrating member distal end in response to distally-biased movement of both the penetrating member and safety shield or probe upon entering the anatomical cavity.

A further object of the present invention is to permit proximal movement of the penetrating member and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of the safety shield or probe upon entering the anatomical cavity.

It is also an object of the present invention to permit proximal movement of the penetrating member and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of the penetrating member upon entering the anatomical cavity.

An additional object of the present invention is to permit proximal movement of the penetrating member and safety shield or probe of a safety penetrating instrument during penetration of an anatomical cavity wall and to utilize both the cannula and safety shield or probe as safety members triggered to move distally from retracted positions exposing the distal end of the penetrating member to extended protruding positions covering the penetrating member distal end in response to distally-biased movement of both the penetrating member and safety shield or probe upon entering the anatomical cavity.

Some of the advantages of the safety penetrating instrument of the present invention are that the distal extending force on a safety member can be designed to assure protrusion of the safety member upon penetration regardless of the anatomical cavity being penetrated, that the force-to-penetrate of a safety penetrating instrument can be minimized to permit use in delicate tissue, that release of the safety member for movement to the extended protruding position can be triggered by distally biased movement of a penetrating member and/or a safety shield or probe in response to penetration of the instrument through the tissue, and that the safety penetrating instrument can be inexpensively manufactured with minimum components to reduce cost, facilitate sterilization for re-use and allow economical single-patient use.

The present invention is generally characterized in a safety penetrating instrument including a penetrating member having a distal end for penetrating an anatomical cavity wall to gain access to an anatomical cavity, a safety member having a distal end movable between an extended position where the safety member distal end is disposed distally of the penetrating member distal end to protect the penetrating member distal end and a retracted position where the safety member distal end is disposed proximally of the penetrating member distal end to expose the penetrating member distal end, extending means for moving the safety member distally to the extended position and for permitting the safety member to move proximally to the retracted position, means for manually moving the safety member proximally from the extended position to the retracted position and locking means for locking the safety member in the retracted position to prevent movement of the safety member to the extended position during penetration of the anatomical cavity wall. The safety member can be a cannula and/or a safety shield or probe biased distally in the retracted position to be movable proximally from the retracted position during penetration of the anatomical cavity wall by the safety penetrating instrument and distally toward the retracted position upon penetration into the anatomical cavity by the safety penetrating instrument. Releasing means responsive to distally-biased movement of the penetrating member and/or the safety shield or probe upon penetration into the anatomical cavity triggers release of the locking means to permit the extending means to move the safety member to the extended position.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 5 is a broken side view, partly in section, of another modification of the safety penetrating instrument according to the present invention.

FIG. 6 is a side view, partly in section, of the distal end of the safety penetrating instrument of FIG. 5 following penetration into the anatomical cavity.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
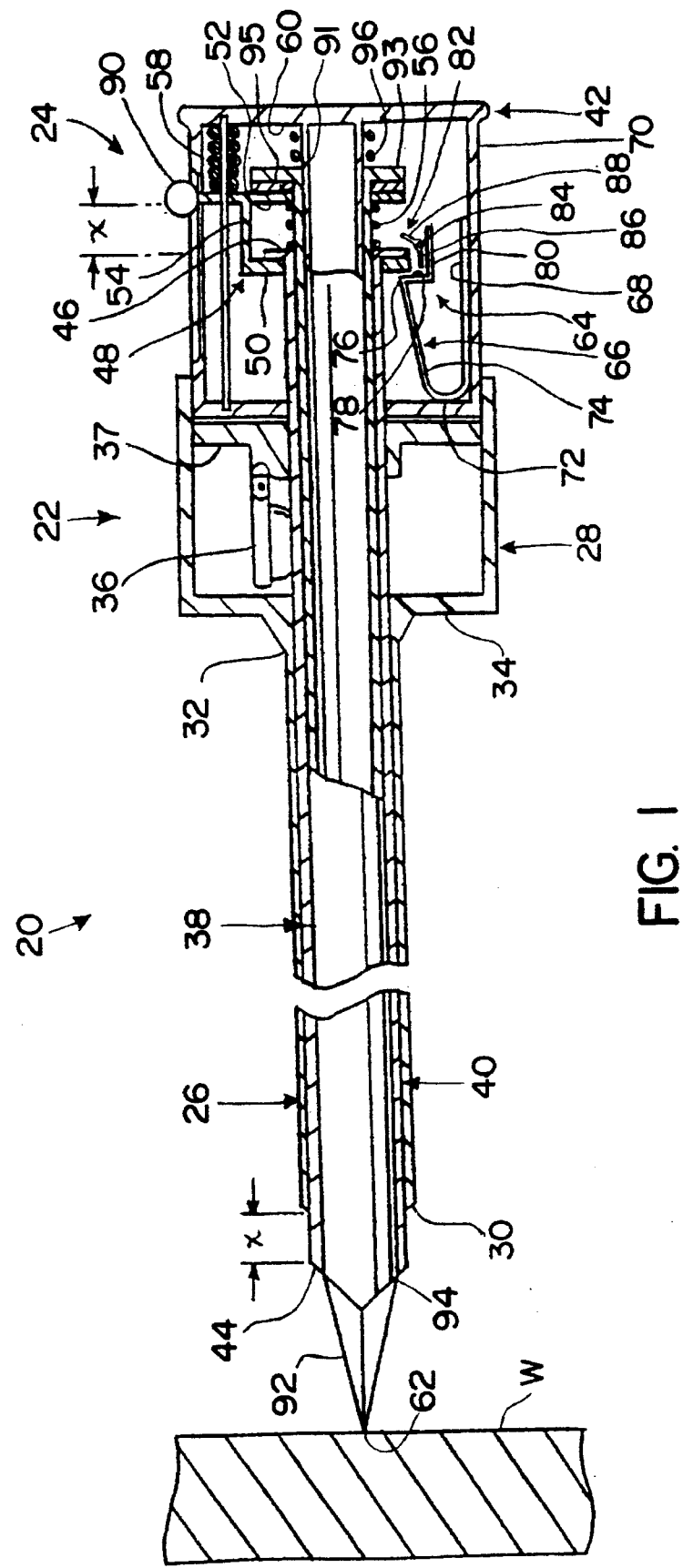
FIG. 1 is a broken side view, partly in section, of a safety penetrating instrument according to the present invention.

A safety penetrating instrument 20 according to the present invention, as shown in FIG. 1, includes a portal unit 22 and a penetrating unit 24. The portal unit 22 includes an elongate portal sleeve, cannula or catheter 26 and a housing 28 mounting a proximal end of portal sleeve 26. Portal sleeve 26 terminates distally at a distal end 30 and proximally at a proximal end 32 secured to front wall 34 of housing 28 and can have any desirable cross-sectional configuration, including cylindrical or tubular configurations, in accordance with the procedure to be performed and the anatomical cavity to be penetrated. Preferably, portal sleeve 26 is made of a substantially cylindrical length of rigid or flexible and transparent or opaque material, such as stainless steel or other medically acceptable plastic or metal material, and has a tubular configuration defining a lumen between the distal and proximal portal sleeve ends for receiving a penetrating member 38 of penetrating unit 24.

Housing 28 can be made of any desirable material and can have any desirable configuration to facilitate grasping by a surgeon and includes a rear wall 37 having an opening therein aligned with an opening in the housing front wall 34 to allow passage therethrough by the penetrating member 38. The housing 28 is preferably constructed to sealingly engage instruments passing therethrough and to include a valve biased to a closed state when no instrument passes through the portal sleeve. A flapper valve 36 is shown; however, any suitable valve construction can be utilized, including trumpet or nipple valves.

Penetrating unit 24 includes penetrating member 38, a safety shield 40 and a hub 42 mounting proximal ends of the penetrating member and the safety shield. Housing 28 defines a rearward-facing recess configured for receiving hub 42; and when the hub is mated with the housing as shown, safety shield 40 is disposed between penetrating member 38 and portal sleeve 26. The safety shield terminates distally at a distal end 44 and proximally at a transverse flange 46 disposed between walls of a rail member 48 mounted in hub 42. Rail member 48 is generally U-shaped including a forward wall 50 disposed transverse or perpendicular to a longitudinal axis of the penetrating instrument, a rearward wall 52 in configuration parallel to forward wall 50 and a side wall 54 transversely joining the forward and rearward rail member walls. Flange 46 is disposed between the rail member forward and rearward walls with the rail member forward wall 50 having an opening therein allowing passage therethrough by the safety shield 40. The rail member forward and rearward walls are disposed parallel or substantially parallel to flange 46, and a bias member 56 is connected between safety shield flange 46 and the rail member rearward wall 52 to bias the safety shield distally. As shown, bias member 56 includes a helical coil spring disposed around the penetrating member 38 and mounted in compression between flange 46 and the rail member rearward wall 52 to bias the safety shield 40 distally to cause flange 46 to abut the rail member forward wall 50. However, bias member 56 can include various other types of springs as well as other types of bias devices including compression springs, tension springs, torsion springs, pan springs, leaf springs, rubber, plastic or magnets, for example. An extending member 58 is mounted between rail member rearward wall 52 and a rear wall 60 of hub 42 to bias the safety shield 40 in a distal direction to an extended protruding position where distal end 44 of the safety shield is disposed beyond a sharp tip of the penetrating member 38 as will be explained further below. The extending member 58 includes a helical coil spring disposed around the penetrating member 38 and mounted in compression between the rail member rearward wall 52 and the hub rearward wall 60 to bias the rail member 48 and, therefore, the safety shield 40, in a distal direction to an extended protruding position where the distal end 44 of the safety shield is disposed beyond the sharp tip 62 of the penetrating member.

A locking and releasing mechanism 64 for locking the safety shield in a retracted position, shown in FIG. 1, exposing the sharp distal tip 62 of the penetrating member and for releasing the rail member 48 to allow the safety shield 40 to move to the extended protruding position includes a latch or locking spring 66, made of a strip of resilient material, formed to have a substantially flat base 68 secured to a bottom wall 70 of hub 42 and a bend 72 joining the base 68 with an upwardly angled arm 74 spaced from the base. Arm 74 carries or forms a latch 76 having a distal angled latching surface joining a proximal latching surface 78 disposed substantially transverse to the longitudinal axis of the safety penetrating instrument and substantially parallel to the rail member forward wall 50. Arm 74 has an extension 80 positioned proximally of latch 76, and a releasing member or trigger 82 is juxtaposed with extension 80. The trigger 82 is pivotally mounted in the hub on a pin 84 secured to a wall or walls of the hub or structure supported in the hub, and the trigger is generally L-shaped with a leg 86 overlying extension 80 and a leg 88 extending transversely from leg 86 but at a slight angle toward the proximal end of the safety penetrating instrument. A torsion spring (not shown) is coiled around pin 84 and fixed to trigger 82 to bias the trigger counterclockwise, looking at FIG. 1, such that leg 86 is biased toward extension 80.

A handle 90 can be coupled with the safety shield 40, such as with flange 46 or rail member 48, for movement along a slot formed in hub 42 to move the safety shield from the extended protruding position to the locked retracted position as previously explained above.

Penetrating member 38 has an elongate shaft or body which is at least partly hollow and is telescopically fitted over a guide tube 91 extending distally from hub rear wall 60. The penetrating member terminates proximally at a transverse flange 93 and has a tapered distal end 92 extending from a transverse dimensional transition 94 in the shaft or body and terminating at the distal tip 62. A bias member 96 in the form of a helical coil spring is disposed around the guide tube 91 and held in compression between the penetrating member flange 93 and the hub rear wall 60 to bias the penetrating member 38 distally toward a transverse wall 95 serving as a stop or abutment limiting distal movement of the penetrating member.

The portal unit 22 and the penetrating unit 24 can be provided separately or assembled together as shown in FIG. 1, and either or both of the portal and penetrating units can be manufactured in a manner to be disposable for single patient use or to be sterilizable for re-use. The hub 42 can be coupled to the housing 28 by suitable detent or latch mechanisms if desired, and the penetrating unit can be withdrawn from the portal unit leaving the portal sleeve 26 in place within an anatomical cavity to serve as a portal for the introduction of medical instruments therethrough.

Figure 3:
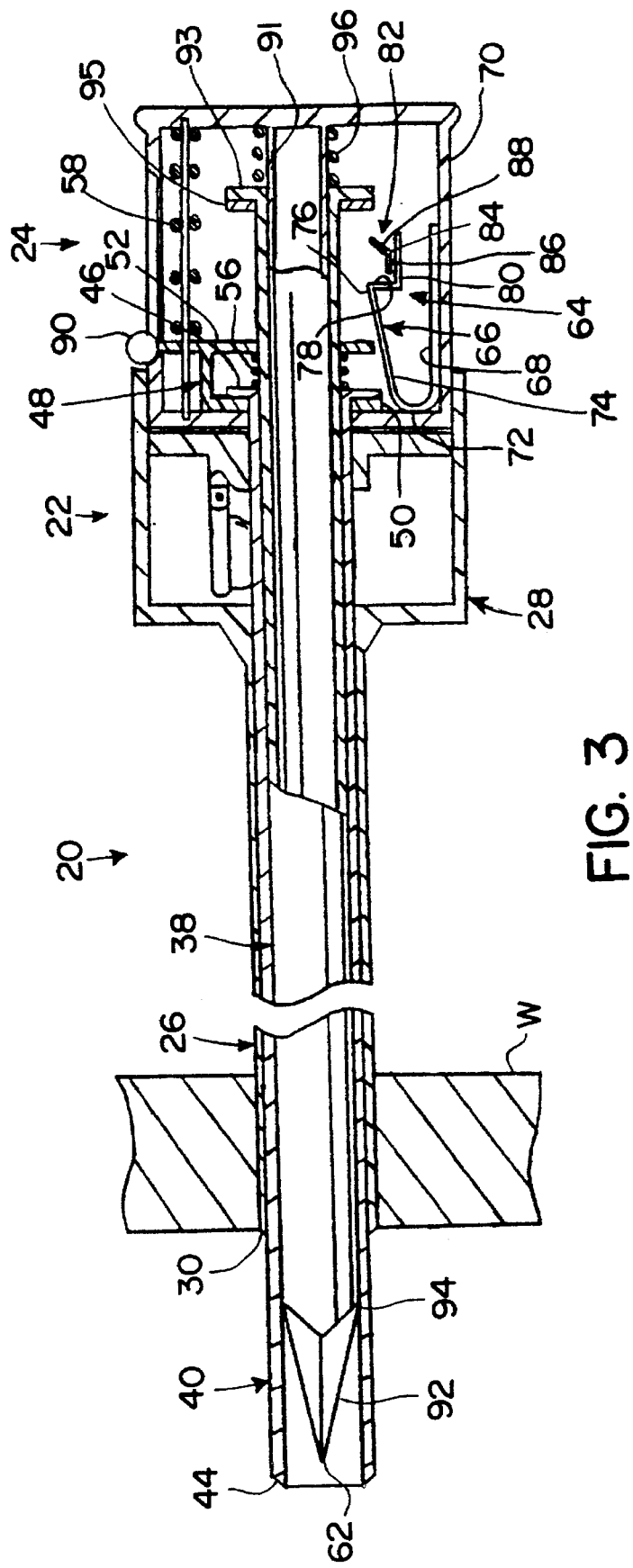
FIG. 3 is a broken side view, partly in section, of the safety penetrating instrument of FIG. 1 following penetration into the anatomical cavity.

In use, the safety shield 40 of safety penetrating instrument 20 will initially be in the extended protruding position shown in FIG. 3 with the safety shield distal end 44 disposed beyond the distal end 92 of penetrating member 38 to protect the sharp tip 62 of the penetrating member. In order to move the safety shield to the retracted position shown in FIG. 1, the handle 90 is grasped to move the safety shield proximally until the rail member forward wall 50 rides over latch 76 to be latched in the retracted position with the rail member forward wall 50 locked against proximal latching surface 78. The user can feel the rail member forward wall 50 lock into place in engagement with the latch 76 and can also visually determine that the safety shield is in the locked retracted position by noting the position of the handle 90 at a proximal end of the slot.

With the safety shield 40 in the locked retracted position illustrated in FIG. 1 and safety shield flange 46 abutting rail member forward wall 50, the distal end 44 of the safety shield 40 will be disposed proximally of the distal tip 62 of the penetrating member in alignment with the transverse dimensional transition 94. Safety shield distal end 44 will also be spaced distally of the portal sleeve distal end 30 a distance x approximately equal to the spacing between rail member forward and rearward walls 50 and 52. When penetration of the cavity wall W is commenced, the force from tissue contact on the distal ends 44 and 92 of the safety shield 40 and penetrating member 38 will cause the safety shield and penetrating member to move proximally against the bias of bias members 56 and 96, respectively, causing the safety shield and penetrating member distal ends to move toward the portal sleeve distal end 30 and causing flange 46 to move past trigger leg 88. Alignment of the portal sleeve and safety shield distal ends 30 and 44 with the penetrating member transition 94 eases penetration. Movement of flange 46 proximally past trigger leg 88 causes trigger 82 to rotate clockwise but does not cause movement of latch 76 since there is no contact of trigger leg 86 with arm extension 80; and, accordingly, flange 46 is now positioned proximally of trigger leg 88 as shown in FIG. 2.

Figure 2:
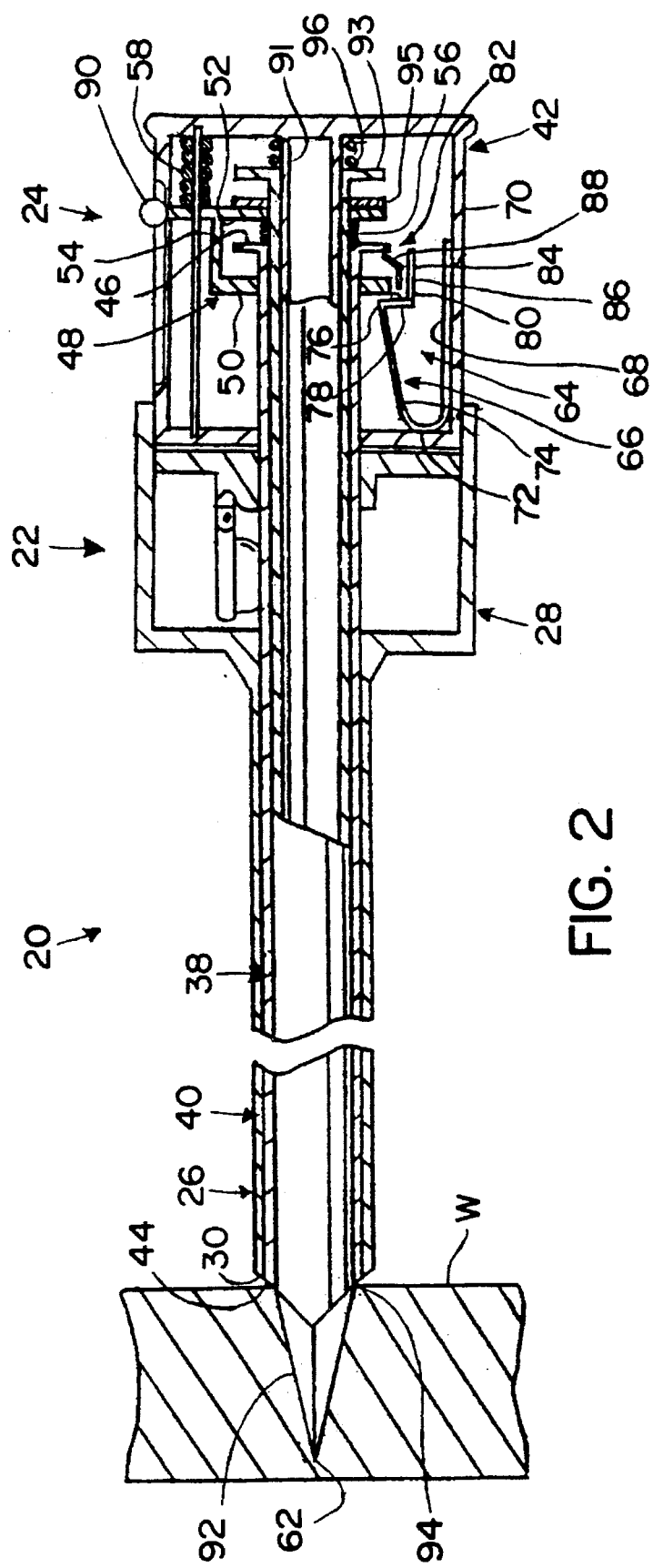
FIG. 2 is a broken side view, partly in section, of the safety penetrating instrument of FIG. 1 during penetration of a wall of an anatomical cavity.

Upon entry into the anatomical cavity, the counter force on the distal ends of the safety shield and penetrating member caused by tissue contact will be reduced allowing bias members 56 and 96 to move the safety shield and penetrating member distally causing flange 46 to engage trigger leg 88 and to pivot the trigger 82 counterclockwise looking at FIG. 2 causing leg 86 to engage arm extension 80. The engagement of leg 86 with arm extension 80 causes latch arm 74 to move toward base 68 moving the latch 76 out of engagement with the rail member forward wall 50 thereby allowing spring 58 to move the safety shield further distally to the extended protruding position wherein the safety shield distal end 44 protrudes beyond the distal end 92 of the penetrating member as shown in FIG. 3. The penetrating unit 24 including the penetrating member 38 and the safety shield 40 can then be withdrawn from the portal unit 22 leaving the portal sleeve 26 in place to serve as a portal for introducing medical instruments into the anatomical cavity.

Figure 4:
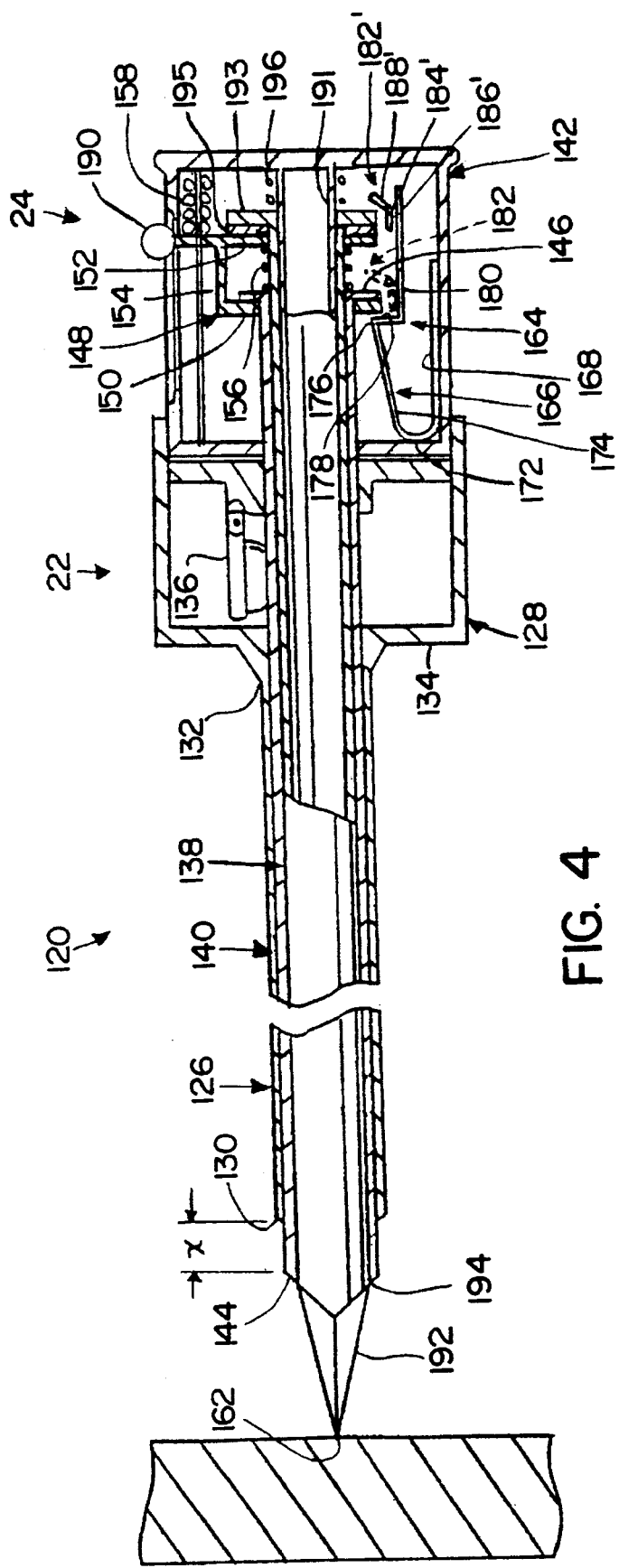
FIG. 4 is a broken side view, partly in section, of a modification of a safety penetrating instrument according to the present invention.

A modification of the safety penetrating instrument of the present invention is shown in FIG. 4 at 120. The modified safety penetrating instrument 120 is similar to safety penetrating instrument 20 except that movement of the safety shield to the extended protruding position is triggered by distal movement of the penetrating member in response to a reduction in the force from tissue contact following entry into the anatomical cavity. Specifically, arm extension 180 for safety penetrating instrument 120 is proximally extended to be disposed alongside penetrating member flange 193 and a trigger 182', similar to trigger 82, is proximally located so that leg 186' is juxtaposed with arm extension 180 and leg 188' is positioned proximally of penetrating member flange 193 when the flange abuts transverse wall 195. Flange 193 moves past trigger leg 188' when penetration of the cavity wall is commenced but does not cause movement of latch 176 since there is no contact of trigger leg 186' with arm extension 180. Upon entry into the anatomical cavity, the counterforce on the distal end of the penetrating member caused by tissue contact is reduced allowing bias member 196 to move the penetrating member 138 distally causing flange 193 to engage trigger leg 188' and to pivot the trigger counterclockwise looking at FIG. 4 causing leg 186' to engage arm extension 180 and latch 176 to move out of engagement with the rail member forward wall 150. The safety shield is then extended in the manner previously described.

Another modification of the safety penetrating instrument of the present invention is arrived at by combining the locking and releasing mechanisms of safety penetrating instruments 20 and 120 to permit movement of the safety shield to the extended protruding position in response to distally-biased movement of either or both of the safety shield and penetrating member. The modification involves mounting a second trigger, shown in phantom at 182 in FIG. 4, distally spaced from trigger 182' for being engaged by safety shield flange 146. With two triggers having legs overlying extension 180, it will be appreciated that the counterclockwise rotation of either trigger will result in latch 176 being moved away from rail member 148 to release the rail member thereby allowing extending member 158 to move the safety shield distally to the extended protruding position in response to distally-biased movement of either the safety shield or the penetrating member.

A further modification of the safety penetrating instrument of the present invention is shown in FIG. 5 at 220 wherein movement of the portal sleeve to an extended protruding position is triggered by distally-biased movement of the safety shield in response to a reduction in the force from tissue contact following entry into the anatomical cavity.

The modified safety penetrating instrument 220 includes a portal unit 222 and a penetrating unit 224. Portal unit 222 includes a portal sleeve 226 similar to portal sleeve 26 but passing through an opening in front wall 234 of housing 228 and terminating proximally at a transverse flange 232. Flange 232 extends toward the upper wall 297 of housing 228, and a pin 298 extends from the flange 232 through a slot 299' to terminate in a handle or knob 290' positioned in an elongate, trough-like recess in the housing upper wall. An extending member 258' is mounted between the portal sleeve flange 232 and the housing rear wall 237 to bias the portal sleeve 226 in a distal direction to an extended protruding position where a distal end 230 of the portal sleeve is positioned beyond the sharp tip 262 of the penetrating member. Extending member 258' is similar to extending member 58 and can include a helical coil spring mounted in compression as shown or any other type of spring or bias device as discussed previously for extending member 58.

A locking and releasing mechanism 264', similar to locking and releasing mechanism 64 but mounted within housing 228, engages the portal sleeve flange 232 to lock the portal sleeve 226 in a retracted position, shown in FIG. 5, exposing the penetrating member distal end 292 and also functions to release the portal sleeve flange 232 allowing the portal sleeve 226 to move to the extended protruding position.

Penetrating unit 224 includes a hub 242 mounting the proximal ends of penetrating member 238 and safety shield 240. Safety shield 240 is similar to safety shield 40 and includes a distal end 244 and a proximal flange 246; however, safety shield flange 246 is disposed between a front wall 259 of the hub and a transverse wall 295 proximally spaced from front wall 259, rather than between the walls of a rail member. In addition, safety shield 240 carries a radial protrusion 245 suitably positioned along the length of the safety shield to be disposed within housing 228 when the hub 242 is mated with the housing 228. Radial protrusion 245 can be a separate member carried on or within the safety shield 240 in a manner to protrude radially therefrom or can be integrally formed as part of the safety shield as shown. The integral protrusion 245 shown is formed from a tongue of material or tab cut from the tubular body of the safety shield 240 and is configured to present a transverse distal abutment surface 247 substantially perpendicular to the longitudinal axis of the safety penetrating instrument. A bend 249 joins the transverse distal abutment surface 247 with an acutely angled proximal abutment surface 251. A bias member 256, similar to bias member 56, is held in compression between the safety shield flange 246 and the transverse wall 295 to distally bias the safety shield 240 toward a rest position where the safety shield flange 246 abuts front wall 259 while permitting proximal movement of the safety shield away from the rest position.

Trigger 282' of locking and releasing mechanism 264' is suitably positioned for being engaged by protrusion 245 rather than by safety shield flange 246. Consequently, trigger leg 288' is proximally spaced from protrusion 245 when the safety shield 240 is in the rest position.

Use of the safety penetrating instrument 220 is similar to that described above for safety penetrating instrument 20 with the exception that safety shield protrusion 245 rather than flange 246 serves as the operating member for engaging the trigger 282'. Prior to penetration, the portal sleeve 226 is in the retracted position, and safety shield 240 and penetrating member 238 are in the rest positions shown in FIG. 5 with the portal sleeve distal end 230 spaced proximally from the safety shield distal end 244 a distance x approximately equal to the distance between the hub front and transverse walls 259 and 295, and safety shield protrusion 245 is located distally of trigger leg 288'.

During penetration, the portal sleeve 226 remains stationary and the safety shield 240 and penetrating member 238 are moved proximally due to the force from tissue contact on their distal ends, and the safety shield protrusion 245 is moved proximally with the safety shield past trigger leg 288' causing trigger 282' to rotate clockwise looking at FIG. 5. Clockwise rotation of the trigger 282' moves trigger leg 286' away from extension 280' and thus does not release the latch 276' holding the portal sleeve flange 232.

Upon penetrating into the anatomical cavity, the counter force on the distal end of the safety shield is reduced allowing bias member 256 to move the safety shield distally causing the vertical abutment surface 247 of the safety shield protrusion 245 to engage trigger leg 288', rotating the trigger 282' counterclockwise. Counterclockwise rotation of trigger 282' causes leg 286' to bear against arm extension 280' moving latch 276' away from portal sleeve flange 232 to release the portal sleeve, thereby allowing extending member 258' to move the portal sleeve to the extended protruding position beyond the penetrating member distal tip 262 as shown in FIG. 6.

Figure 7:
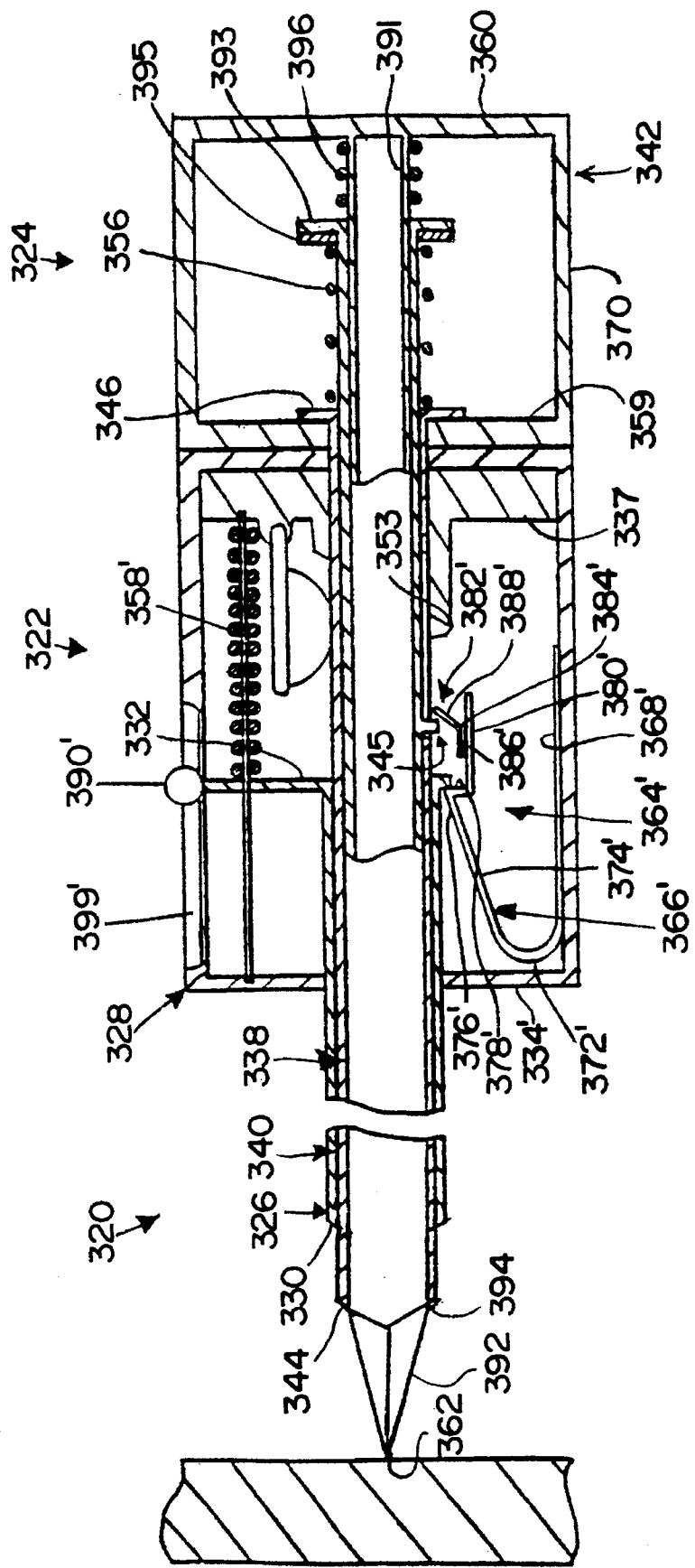
FIG. 7 is a broken side view, partly in section, of a further modification of a safety penetrating instrument according to the present invention.

Yet another modification of the safety penetrating instrument of the present invention is shown in FIG. 7 wherein the modified safety penetrating instrument 320 is similar to safety penetrating instrument 220 with the exception of the portal sleeve being triggered to move distally from the retracted position exposing the penetrating member distal end to the extended protruding position beyond the distal end of the penetrating member in response to distally-biased movement of the penetrating member following penetration into the anatomical cavity.

Portal unit 322 and penetrating unit 324 for safety penetrating instrument 320 are essentially the same as portal unit 222 and penetrating unit 224 for safety penetrating unit 220; however, safety shield 340 is slotted at 353 and penetrating member 338 carries a radial protrusion 345 extending through the slot 353 into housing 328. Slot 353 extends along a longitudinal axis of the safety shield 340 and is sufficiently long to permit the radial protrusion 345 to move along the slot without obstruction when the penetrating member 338 and safety shield 340 move relative to one another. When penetrating member 338 is in the rest position shown in FIG. 7, the penetrating member flange 393 abuts transverse wall 395 and radial protrusion 345 is located distally of trigger leg 388'. Proximal movement of penetrating member 338 caused by tissue resistance during penetration moves protrusion 345 proximally along slot 353 and past trigger leg 388'. Upon penetrating into the anatomical cavity, the force from tissue contact is reduced allowing bias member 396 to move the penetrating member 338 distally. Protrusion 345 is carried along with penetrating member 338 in a distal direction and engages leg 388' to rotate the trigger 382' counterclockwise. Latch 376' is thus released from portal sleeve flange 332 allowing extending member 358' to move the portal sleeve to the extended protruding position previously shown in FIG. 6.

Figures 8, 9:
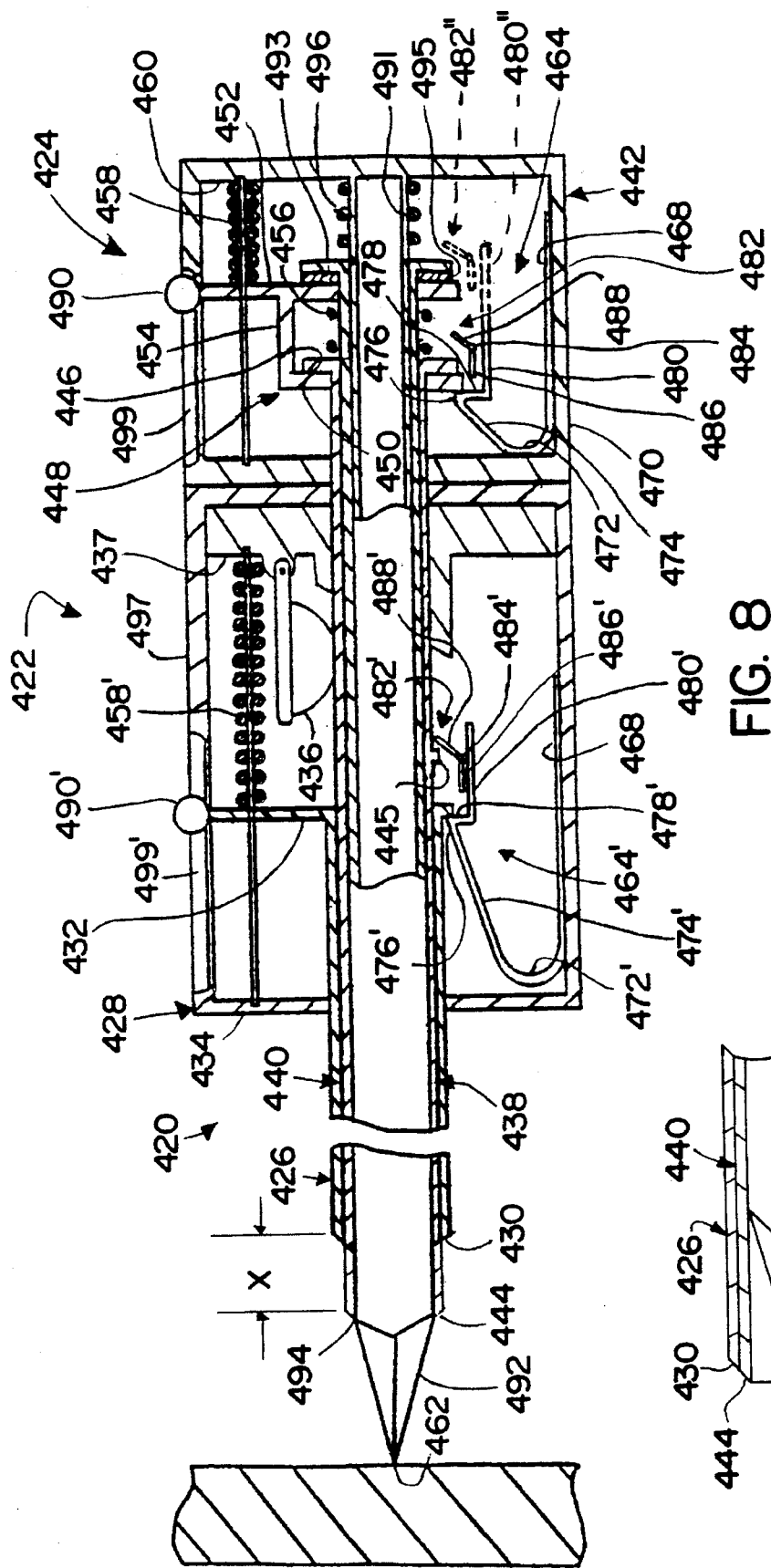
FIG. 8 is a broken side view, partly in section, of another modification of the safety penetrating instrument of the present invention.
FIG. 9 is a side view, partly in section, of the distal end of the safety penetrating instrument of FIG. 8 following penetration through an anatomical cavity wall.

Yet another modification of the safety penetrating instrument of the present invention is illustrated in FIG. 8 wherein the modified safety penetrating instrument 420 is similar to safety penetrating instrument 320 with the exception that both the portal sleeve and safety shield are triggered to move distally from retracted positions exposing the penetrating member distal end to extended protruding positions beyond the distal tip of the penetrating member in response to distally-biased movement of the safety shield upon penetrating into an anatomical cavity. Safety penetrating instrument 420 includes a portal unit 422 similar to portal unit 322 for safety penetrating instrument 320 and a penetrating unit 424 similar to penetrating unit 24 for safety penetrating instrument 20. Additionally, safety shield 440 includes a radial protrusion 445 like radial protrusion 345 for safety penetrating instrument 320.

Locking and releasing mechanism 464' for safety penetrating instrument 420 is mounted within housing 428 for engaging the portal sleeve flange 432 and a similar locking and releasing mechanism 464 is mounted within the hub 442 for engaging the safety shield rail member 448. Similarly, an extending member 458' is held in compression between the portal sleeve flange 432 and the housing rear wall 437, and another extending member 458 is held in compression between rail member rearward wall 452 and the rear wall 460 of the hub. Bias member 456 for the safety shield is mounted between the safety shield proximal flange 446 and the rail member rearward wall 452 allowing the safety shield to move proximally during penetration; and, upon penetrating into an anatomical cavity, distally-biased movement of the safety shield causes protrusion 445 and safety shield flange 446 to engage triggers 482 and 482' thereby releasing the portal sleeve and safety shield to be moved distally to extended positions.

Use of the safety penetrating instrument 420 proceeds essentially as previously described with the exception that both the portal sleeve and safety shield must be retracted prior to use in order to expose the penetrating member distal end. Handles 490' and 490 are coupled with the portal sleeve and safety shield, respectively, for this purpose and can be grasped and moved proximally together or individually to move the portal sleeve and safety shield from their extended positions shown in FIG. 9 to the retracted positions shown in FIG. 8. Once the safety shield rail member and portal sleeve flange have been locked, penetration of the anatomical cavity wall can be commenced as previously described.

Another modification of the safety penetrating instrument of the present invention is arrived at by mounting a third trigger, shown in phantom at 482" in FIG. 8, distally spaced from trigger 482 for being engaged by the penetrating member flange 493. With two triggers having legs overlying arm extension 480, it will be appreciated that the counter-clockwise rotation of either trigger will result in latch 476 being moved away from rail member 448 to release the rail member and safety shield thereby allowing extending member 458 to move the safety shield distally to the extended protruding position in response to distally-biased movement of either the safety shield or the penetrating member.

Figure 10:
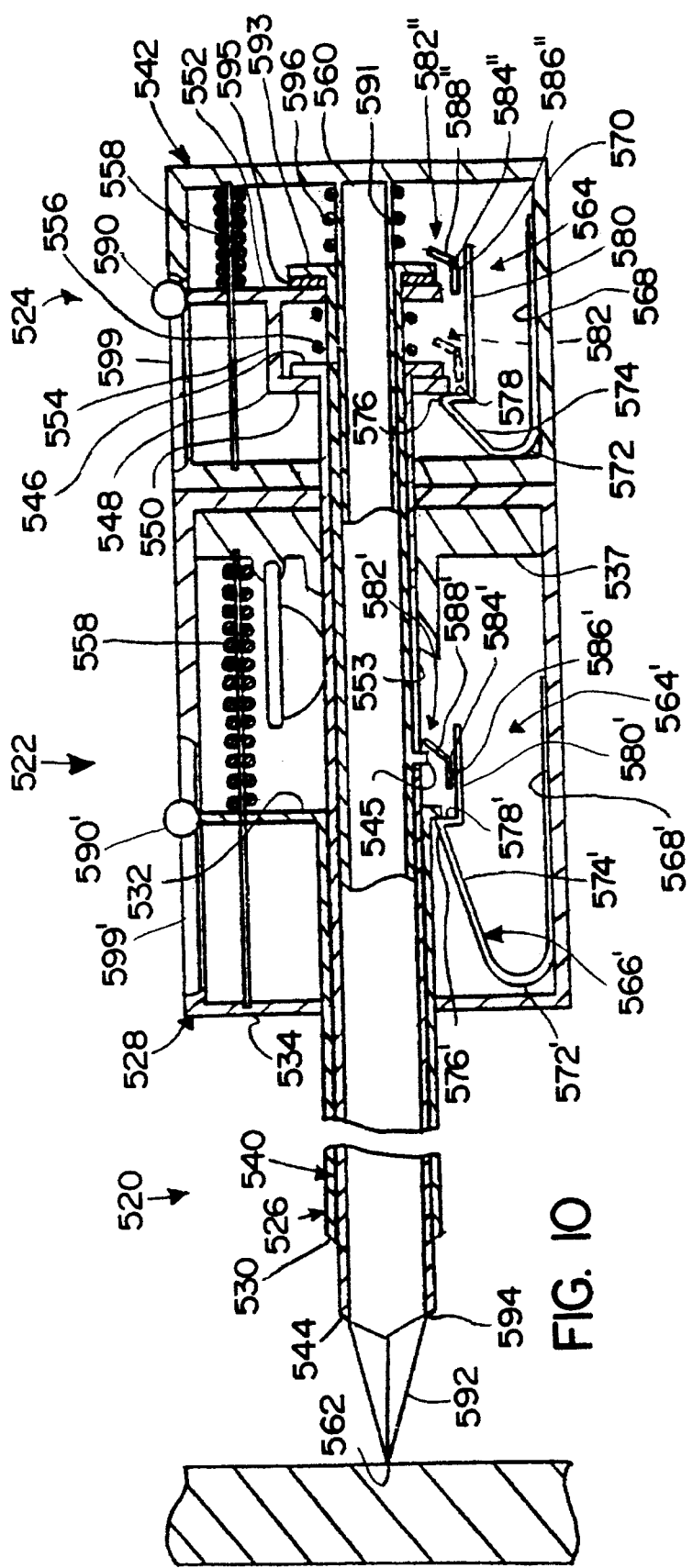
FIG. 10 is still another modification of the safety penetrating instrument of the present invention.

FIG. 10 illustrates yet another modification of the safety penetrating instrument of the present invention wherein movement of the portal sleeve and safety shield to extended protruding positions is triggered by distally-biased movement of the penetrating member. The portal unit 522 for safety penetrating instrument 520 is the same as portal unit 322, so that movement of the portal sleeve 526 to an extended protruding position is triggered by distally-biased movement of the penetrating member 538. Penetrating unit 524 is similar to penetrating unit 424 but with the penetrating member 538 carrying a radial protrusion 545 extending through a slot 553 in safety shield 540 and only one trigger 582" having a lower leg 586" overlying extension 580 of latch 576 and an upper leg 588" proximally spaced from penetrating member flange 593 when the penetrating member is in a rest position with the penetrating member flange 593 abutting the hub transverse wall 595. Operation of the safety penetrating instrument 520 is essentially the same as for safety penetrating instrument 420 with the exception that the radial protrusion 545 and flange 593 of the penetrating member function as the operating members for triggering release of locking and releasing mechanisms 564' and 564 holding the portal sleeve 526 and safety shield 540, respectively.

In the embodiments shown, the distal end of the portal sleeve is proximally spaced from the distal end of the safety shield prior to use and is held stationary during penetration. The distal end of the safety shield is aligned with a transverse dimensional transition along the longitudinal axis of the penetrating member at the penetrating member distal end when the safety shield and penetrating member are in retracted or rest positions immediately prior to use in penetrating the anatomical cavity wall; and since both the penetrating member and safety shield are movable proximally during penetration, the distal ends of the penetrating member and safety shield can move into alignment with the distal end of the portal sleeve during penetration, with one or both of the penetrating member and safety shield triggering protrusion of a safety member when moving distally toward the aligned position upon entering the anatomical cavity.

Figure 11:
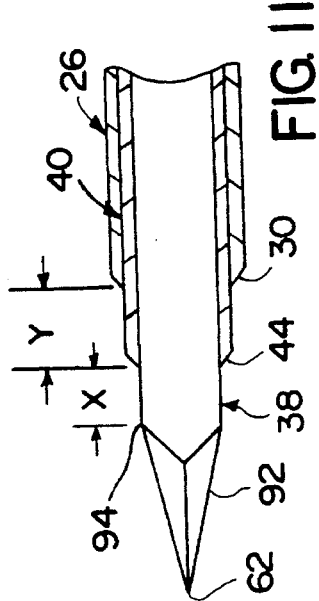

FIG. 11 shows an alternative distal configuration for the safety penetrating instruments of the present invention wherein the safety shield distal end 44 is located proximally of the penetrating member distal end transition 94 a predetermined distance x prior to use and the portal sleeve distal end 30 is spaced proximally from the safety shield distal end 44 a predetermined distance y. In this configuration the safety shield will begin to move proximally after the penetrating member 38 has penetrated the anatomical cavity wall to a predetermined depth x and will move alone or together with the penetrating member towards becoming aligned with the portal sleeve distal end 30. Upon entering into the anatomical cavity, the penetrating member and safety shield spring back to the original positions shown in FIG. 11 thereby triggering protrusion of the portal sleeve and/or safety shield beyond the penetrating member distal end 92 to function as safety members.

Figure 12:
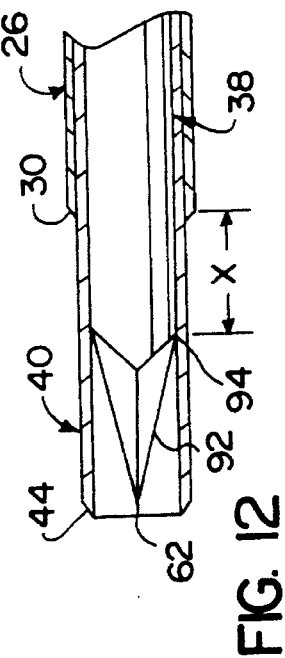
FIGS. 11 and 12 are side views, partly in section, of alternative distal configurations for the safety penetrating instrument of the present invention.

FIG. 12 shows an alternative distal configuration for the safety penetrating instruments of the present invention wherein the distal end 44 of the safety shield 40 is spaced distally from the penetrating member distal end transition 94 prior to use and the portal sleeve distal end 30 is spaced proximally of the penetrating member distal transition 94 a predetermined distance x. In this configuration the safety shield distal end 44 will move proximally during penetration towards becoming aligned with the penetrating member transition 94 and will move proximally with the penetrating member until the safety penetrating instrument enters the anatomical cavity. The penetrating member and safety shield will spring back towards their original positions upon entering into the anatomical cavity thereby triggering protrusion beyond the penetrating member distal end 92 by the portal sleeve and/or the safety shield.

From the above, it will be appreciated that the penetrating member and safety shield of the safety penetrating instrument of the present invention are movable proximally during penetration of an anatomical cavity wall and distally upon entering the anatomical cavity to trigger further distal movement of the safety shield and/or protrusion of a cannula, such as a portal sleeve, to function as safety members protecting the distal end of the penetrating member. By "safety member" is meant any structure moveable distally relative to the penetrating member to protect the tip of the penetrating member within an anatomical cavity. Since in the safety penetrating instrument of the present invention one or both of a cannula and safety shield can be extended to protect the penetrating member tip, each can function as a safety member upon penetration of the safety penetrating instrument into an anatomical cavity. The cannula, whether or not it functions as a safety member, can be a portal sleeve, a needle open at both ends with fluid flow therethrough, a catheter or any other tubular component of a medical instrument. When the cannula is not triggered to protrude as a safety member, it is coupled with a safety member such as a tubular safety shield disposed between the cannula and a penetrating member, a safety probe fitted within a hollow penetrating member, or a component partly within and around the penetrating member and movable distally to protrude relative to the penetrating member to protect the distal end thereof when triggered. On the other hand, if the cannula does function as a safety member, it can be coupled with a protective sheath or probe that is not triggered to protrude or with any of the aforementioned safety members. Redundant safety can also be achieved by biasing the cannula, safety shield and/or penetrating member distally while allowing one or more of the members to move proximally during penetration and triggering protrusion of the safety member in response to distal movement of one or more of the cannula, the safety shield and the penetrating member upon entry into the anatomical cavity. Additionally, the triggered safety member protrusion can be combined with penetrating member retraction to provide separate modes of safety.

The components of the safety penetrating instrument of the present invention can be made of any suitable, medical grade materials to permit sterilization for re-use or for single patient use. The components can be made of multiple parts of various configurations and materials to reduce cost. The portal unit can have various valves, stop cocks and seals in the housing to control fluid flow therethrough, and conventional detent mechanisms can be used to connect or latch the hub with the housing when the portal unit and the penetrating unit are assembled. The distal ends of the cannula and the safety shield can be chamfered or blunt, smooth or roughened, or have any other configuration depending on the need for ease of penetration or increased resistance. Further, the safety shield can be mounted either by the portal unit or the penetrating unit depending on the desirability of being left in place within the portal sleeve or withdrawn with the penetrating member.

Figure 13:
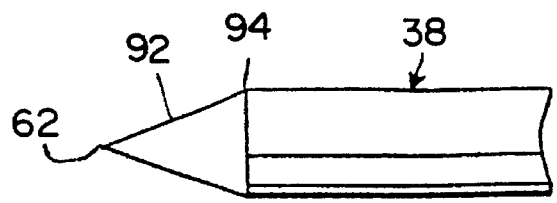
FIGS. 13–18 are side views of alternative distal configurations for the penetrating member of the safety penetrating instrument of the present invention.
Figure 14:
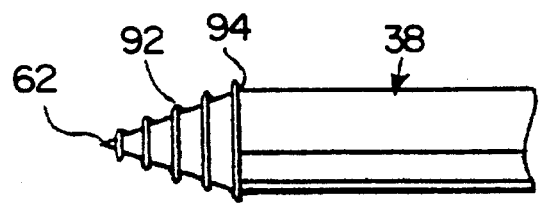
Figure 15:
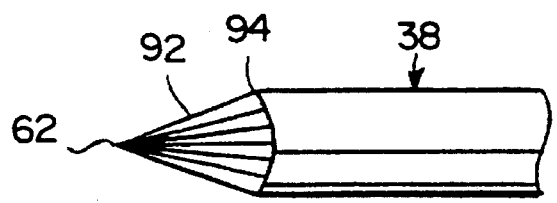
Figure 16:
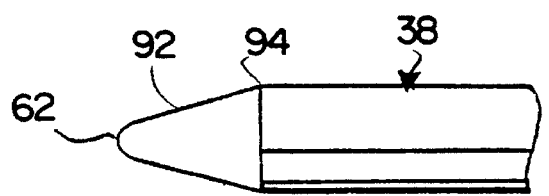
Figure 17:
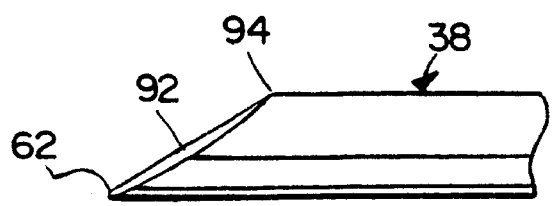
Figure 18:
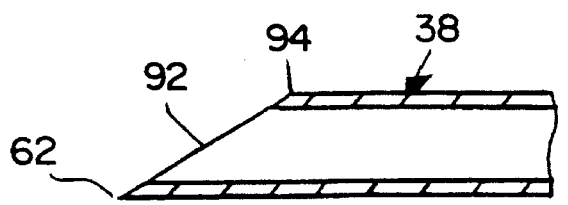

The penetrating member can be solid, hollow or partially solid and hollow, formed as single or multiple pieces, and fixed or movable telescopically over a guide tube or the like. The distal end 92 of the penetrating member 38 can have any configuration desired for a particular procedure, for example, the pyramidal trocar configuration shown or a conical distal end (FIG. 13), a threaded distal end (FIG. 14), a multifaceted distal end (i.e., having two or more facets as shown in FIG. 15), a blunt distal end (FIG. 16), a slanted distal end (FIG. 17) or a hollow needle configuration (FIG. 18) with fluid flow therethrough to communicate with various valves, stop cocks and seals in the hub. Additionally, the surface defining the distal end of the penetrating member can be irregular or smooth, continuous or perforated, provided with cutting features or having any combination of the above. If the penetrating member 38 is a hollow needle having a beveled end 92 as shown or a curved Tuohey-type distal configuration, the proximal edge of the opening at the distal end of the needle is considered the transverse dimensional transition 94 and thus the cannula and/or safety shield distal end is aligned with the distal end of the needle when located adjacent the proximal edge.

Figure 19:
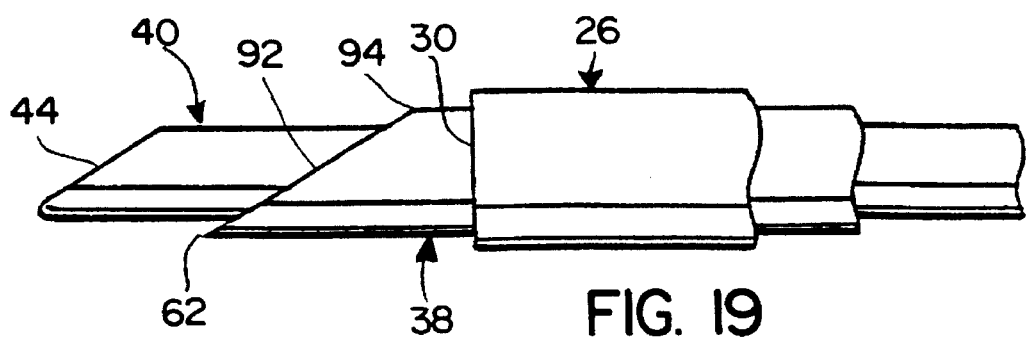
FIG. 19 is a side view, partly in section, of the distal end of a penetrating member configured to accommodate a safety probe.

As mentioned previously, the safety member of the present invention can be a tubular member such as a cannula or a safety shield disposed between the cannula and a penetrating member, or in the case of a hollow penetrating member, the safety member can be a probe disposed at least partially within the penetrating member and movable through one or more apertures formed at or near the distal end of the penetrating member. FIG. 19 shows a cannula 26 surrounding a hollow penetrating member 38 with a beveled distal opening 92 and a cylindrical safety probe 40 in an extended protruding position to protect the distal tip 62 of the penetrating member. The safety probe has a beveled distal end 44 and is preferably movable from the extended position shown to a retracted position where the beveled distal end 44 of the safety probe 40 is flush with the distal end 92 of the penetrating member 38. It will be appreciated that a coaxial extending mechanism can be fitted within the penetrating member to move the safety probe to the extended position or a flange can be carried at the safety probe proximal end and passed through a slot or opening in the penetrating member to be acted on by any of the extending mechanisms previously described. The safety probe distal end 44 can have any configuration to protrude through single or multiple openings formed in the penetrating member distal end 92 and can conform to the distal profile of the penetrating member or present a discontinuous surface when retracted.

The rail members used herein can have various configurations to engage a latch and be released by a trigger. Preferably, each rail member will have a configuration to serve as a stop or abutment for an operating member as exemplified herein by a U-shaped rail member.

The locking and releasing mechanisms require only a latch for locking the safety member in the retracted position and a trigger for releasing the latch in response to distal movement of an operating member; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety penetrating instrument of the present invention are disclosed in Applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07/945,177, filed Sep. 15, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference. The above applications disclose automatically retracting safety penetrating instruments such that modification of the locking and releasing mechanisms requires configuring the latches to lock a member in a retracted position rather than in an extended position. The above applications also disclose various bias arrangements useful with the safety penetrating instrument of the present invention. Other locking and releasing mechanisms that can be used in the safety penetrating instrument of the present invention are disclosed in Applicant's pending applications Ser. Nos. 08/279,170 and 08/279,172, filed Jul. 22, 1994, the disclosures of which are incorporated herein by reference.

One or more control buttons, such as the control buttons described in Applicant's copending patent application, Ser. No. 08/083,220, filed Jun. 24, 1993, can be mounted next to any latch for manually disengaging the latch to prevent locking of the safety member in the retracted position, in some cases converting the safety penetrating instrument to a standard safety shielded penetrating instrument without triggered protrusion. In addition, any latch can carry a secondary pawl or protrusion at a distal end for locking the safety member in the extended position and can then be released through the use of a control button as described above.

The transverse or radial protrusions 245, 345, 445 and 545 carried by the safety shield 40 and/or penetrating member 38 can be integrally formed on an exterior surface of the safety shield or penetrating member as shown or can be mounted within the safety shield or penetrating member as part of a pivoted lever protruding through slots in the penetrating member 38 and safety shield 40 to engage the triggers in their respective housings. If part of a pivoted lever, the protrusions can be made to withdraw into their respective penetrating members by rotating the lever, for example by use of a control button positioned adjacent the lever and operable to cam the lever in a manner to withdraw the protrusion.

It will also be appreciated that the safety penetrating instrument of the present invention permits use of strong bias springs to ensure movement of the safety member (whether it be the cannula, a safety shield or probe, or both) to the extended protruding position without increasing the force to penetrate. After penetration of the safety penetrating instrument into the anatomical cavity, the safety member acts as a shock absorber upon inadvertent contact with tissue which contact can be felt by the surgeon and visually determined by movement of the handle. The distal bias for the triggering member (i.e., the penetrating member and/or safety shield or probe) of the safety penetrating instrument need only be strong enough to allow slight movement of the member during penetration such that the force-to-penetrate can be minimized. The features of the various embodiments described above can be combined in any manner desired dependent upon the requirements and complexity of the safety penetrating instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall, said penetrating member being movable relative to said housing between an extended rest position and a penetrating member retracted position;

a safety member disposed within said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

safety member extending means for moving said safety member distally relative to said housing from said safety member retracted position to said safety member extended position;

means for manually moving said safety member proximally relative to said housing from said safety member extended position to said safety member retracted position;

safety member locking means for locking said safety member in said safety member retracted position to prevent distal movement of said safety member relative to said housing beyond said safety member retracted position while permitting proximal movement of said safety member relative to said housing during penetration of the anatomical cavity wall;

safety member bias means for biasing said safety member distally relative to said housing in said safety member retracted position and for permitting proximal movement of said safety member relative to said housing from said safety member retracted position during penetration of the anatomical cavity wall and distal movement of said safety member relative to said housing toward said safety member retracted position upon introduction into the anatomical cavity;

penetrating member bias means for biasing said penetrating member distally relative to said housing toward said penetrating member rest position and for permitting proximal movement of said penetrating member relative to said housing during penetration of the anatomical cavity wall; and releasing means responsive to penetration of said safety penetrating instrument into the anatomical cavity for triggering release of said safety member locking means to permit said safety member extending means to move said safety member distally relative to said housing from said safety member retracted position to said safety member extended position.

2. A safety penetrating instrument as recited in claim 1 wherein said releasing means is responsive to distally-biased movement of said safety member upon penetrating into the anatomical cavity.

3. A safety penetrating instrument as recited in claim 1 wherein said releasing means is responsive to distally-biased movement of said penetrating member upon penetrating into the anatomical cavity.

4. A safety penetrating instrument as recited in claim 1 wherein said releasing means is responsive to distally-biased movement of said safety member and said penetrating member upon penetrating into the anatomical cavity.

5. A safety penetrating instrument as recited in claim 1 wherein said safety member is a tubular safety shield disposed between said penetrating member and said cannula.

6. A safety penetrating instrument as recited in claim 1 wherein said penetrating member is at least partly hollow and said safety member is a safety probe disposed within said penetrating member.

7. A safety penetrating instrument as recited in claim 1 wherein said cannula distal end is spaced proximally from said safety member distal end when said safety member distal end is in said retracted position.

8. A safety penetrating instrument as recited in claim 7 wherein said penetrating member distal end extends distally from a transverse dimensional transition in said penetrating member and said safety member distal end is aligned with said transition when in said retracted position.

9. A safety penetrating instrument as recited in claim 7 wherein said penetrating member distal end extends distally from a transverse dimensional transition in said penetrating member and said safety member distal end is located proximally of said transition when in said retracted position.

10. A safety penetrating instrument as recited in claim 7 wherein said penetrating member distal end extends distally from a transverse dimensional transition in said penetrating member and said safety member distal end is located distally of said transition when in said retracted position.

11. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

a safety member disposed within said cannula and having a distal end, said safety member being movable relative to said housing between a safety member rest position and safety member retracted position where said safety member distal end is proximally spaced from said penetrating member distal end;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

means for manually moving said cannula proximally relative to said housing from said cannula extended position to said cannula retracted position;

cannula locking means for locking said cannula in said cannula retracted position to prevent movement of said cannula relative to said housing during penetration of the anatomical cavity wall;

safety member bias means for biasing said safety member distally relative to said housing toward said safety member rest position and for permitting proximal movement of said safety member relative to said housing during penetration of the anatomical cavity wall;

penetrating member bias means for biasing said penetrating member distally relative to said housing toward a penetrating member rest position and for permitting proximal movement of said penetrating member relative to said housing during penetration of the anatomical cavity wall; and releasing means responsive to penetration of said safety penetrating instrument into the anatomical cavity for triggering release of said cannula locking means to permit said cannula extending means to move said cannula distally relative to said housing from said cannula retracted position to said cannula extended position.

12. A safety penetrating instrument as recited in claim 11 wherein said releasing means is responsive to distally-biased movement of said safety member upon penetrating into the anatomical cavity.

13. A safety penetrating instrument as recited in claim 11 wherein said releasing means is responsive to distally-biased movement of said penetrating member upon penetrating into the anatomical cavity.

14. A safety penetrating instrument as recited in claim 11 wherein said releasing means is responsive to distally-biased movement of said safety member and said penetrating member upon penetrating into the anatomical cavity.

15. A safety penetrating instrument as recited in claim 11 wherein said safety member is a tubular safety shield disposed between said penetrating member and said cannula.

16. A safety penetrating instrument as recited in claim 11 wherein said penetrating member is at least partly hollow and said safety member is a safety probe disposed within said penetrating member.

17. A safety penetrating instrument as recited in claim 11 wherein said penetrating member distal end extends distally from a transverse dimensional transition in said penetrating member and said cannula distal end is located proximally of said transition when said cannula is in said retracted position and said penetrating member is in said rest position.

18. A safety penetrating instrument as recited in claim 17 wherein said safety member distal end is spaced distally of said cannula distal end when said safety member is in said rest position and said cannula is in said retracted position.

19. A safety penetrating instrument as recited in claim 18 wherein said safety member distal end is aligned with said penetrating member distal transition when said safety member and penetrating member are in rest positions.

20. A safety penetrating instrument as recited in claim 18 wherein said safety member distal end is proximally spaced from said penetrating member transition when said safety member and penetrating member are in rest positions.

21. A safety penetrating instrument as recited in claim 18 wherein said safety member distal end is distally spaced from said penetrating member distal transition when said safety member and penetrating member are in rest positions.

22. A safety penetrating instrument for establishing a portal in the wall of an anatomical cavity comprising a housing;

an elongate cannula mounted by said housing and having a distal end for introduction in the anatomical cavity and a proximal end for positioning externally of the anatomical cavity;

a penetrating member disposed in said cannula and having a distal end for penetrating the anatomical cavity wall;

a safety member disposed within said cannula and having a distal end, said safety member being movable relative to said housing between a safety member extended position where said safety member distal end protrudes distally from said penetrating member distal end and a safety member retracted position where said safety member distal end is disposed proximally of said penetrating member distal end to expose said penetrating member distal end;

cannula extending means for moving said cannula distally relative to said housing from a cannula retracted position where said cannula distal end is disposed proximally of said penetrating member distal end to a cannula extended position where said cannula distal end protrudes distally from said penetrating member distal end;

safety member extending means for moving said safety member distally relative to said housing from said safety member retracted position to said safety member extended position;

means for manually moving said cannula proximally relative to said housing from said cannula extended position to said cannula retracted position;

means for manually moving said safety member proximally relative to said housing from said safety member extended position to said safety member retracted position;

cannula locking means for locking said cannula in said cannula retracted position and to prevent movement of said cannula relative to said housing during penetration of the anatomical cavity wall;

safety member locking means for locking said safety member in said safety member retracted position to prevent movement of said safety member distally relative to said housing from said safety member retracted position to said safety member extended position while permitting proximal movement of said safety member relative to said housing from said safety member retracted position during penetration of the anatomical cavity wall;

safety member bias means for biasing said safety member distally relative to said housing in said safety member retracted position to permit said safety member to move proximally relative to said housing from said safety member retracted position during penetration of the anatomical cavity wall and distally relative to said housing toward said safety member retracted position upon introduction into the anatomical cavity;

penetrating member bias means for biasing said penetrating member distally relative to said housing toward an extended rest position and for permitting said penetrating member to move proximally relative to said housing from said penetrating member rest position during penetration of the anatomical cavity wall; and releasing means responsive to penetration of said safety penetrating instrument into the anatomical cavity for triggering release of said safety member and said cannula locking means to permit said safety member extending means and said cannula extending means to move said safety member and said cannula distally relative to said housing from said respective retracted positions to said respective extended positions.

23. A safety penetrating instrument as recited in claim 22 wherein said releasing means is responsive to distally-biased movement of said safety member upon penetrating into the anatomical cavity.

24. A safety penetrating instrument as recited in claim 22 wherein said releasing means is responsive to distally-biased movement of said penetrating member upon penetrating into the anatomical cavity.

25. A safety penetrating instrument as recited in claim 22 wherein said releasing means is responsive to distally-biased movement of said safety member and said penetrating member upon penetrating into the anatomical cavity.

26. A safety penetrating instrument as recited in claim 22 wherein said safety member is a tubular safety shield disposed between said penetrating member and said cannula.

27. A safety penetrating instrument as recited in claim 22 wherein said penetrating member is at least partly hollow and said safety member is a safety probe disposed within said penetrating member.

28. A safety penetrating instrument as recited in claim 22 wherein said penetrating member distal end extends distally from a transverse dimensional transition in said penetrating member and said cannula distal end is located proximally of said transition when in said retracted position.

29. A safety penetrating instrument as recited in claim 28 wherein said safety member distal end is spaced distally of said cannula distal end when said safety member and cannula are retracted.

30. A safety penetrating instrument as recited in claim 29 wherein said safety member distal end is aligned with said penetrating member distal transition when said safety member is retracted and said penetrating member is in said rest position.

31. A safety penetrating instrument as recited in claim 29 wherein said safety member distal end is spaced proximally of said penetrating member distal transition when said safety member is retracted and said penetrating member is in said rest position.

32. A safety penetrating instrument as recited in claim 29 wherein said safety member distal end is spaced distally from said penetrating member distal transition when said safety member is retracted and said penetrating member is in said rest position.

* * * * *